(12) United States Patent
Lauer et al.

(10) Patent No.: US 7,217,364 B2
(45) Date of Patent: May 15, 2007

(54) FILTERING DEVICE AND A FILTERING DEVICE HOUSING

(75) Inventors: Martin Lauer, St. Wendel (DE); Uwe Hahmann, Tiefenbronn (DE); Gerhard Wiesen, Eppstein (DE)

(73) Assignee: Fresenius Medical Care Deutschland GmbH, Bad Homburg (DE)

( * ) Notice: Subject to any disclaimer, the term of this patent is extended or adjusted under 35 U.S.C. 154(b) by 281 days.

(21) Appl. No.: 10/491,135

(22) PCT Filed: Jul. 26, 2002

(86) PCT No.: PCT/EP02/08357

§ 371 (c)(1), (2), (4) Date: Mar. 29, 2004

(87) PCT Pub. No.: WO03/028859

PCT Pub. Date: Apr. 10, 2003

(65) Prior Publication Data

US 2004/0262212 A1 Dec. 30, 2004

(30) Foreign Application Priority Data

Sep. 28, 2001 (DE) ............... 101 47 903

(51) Int. Cl.
*B01D 63/02* (2006.01)
*B01D 29/00* (2006.01)

(52) U.S. Cl. ............ 210/321.79; 210/321.8; 210/321.88; 210/321.89; 210/446; 210/455; 210/500.23; 422/44

(58) Field of Classification Search ........... 210/321.6, 210/321.72, 321.79, 321.8, 321.88, 321.89, 210/455, 456, 500.23, 446; 422/44
See application file for complete search history.

(56) References Cited

U.S. PATENT DOCUMENTS

| | | | | |
|---|---|---|---|---|
| 3,442,388 A | * | 5/1969 | Pall | 210/321.77 |
| 4,080,295 A | * | 3/1978 | Riede | 210/321.72 |
| 4,211,597 A | | 7/1980 | Lipps et al. | |
| 5,395,468 A | * | 3/1995 | Juliar et al. | 156/169 |
| 5,514,335 A | * | 5/1996 | Leonard et al. | 422/46 |
| 5,866,001 A | * | 2/1999 | Hlebovy | 210/321.6 |
| 6,024,918 A | * | 2/2000 | Hendriks et al. | 422/44 |
| 6,207,053 B1 | * | 3/2001 | Carroll et al. | 210/500.23 |
| 6,258,321 B1 | * | 7/2001 | Van Driel et al. | 422/44 |
| 6,426,002 B1 | * | 7/2002 | Hahmann et al. | 210/321.79 |

FOREIGN PATENT DOCUMENTS

| | | |
|---|---|---|
| DE | 33 21 038 C2 | 11/1984 |
| DE | 100 23 427 A1 | 11/2001 |
| EP | 0 887 100 A1 | 12/1998 |
| FR | 2 546 414 | 11/1984 |
| WO | 94/23828 | 10/1994 |
| WO | 01/08722 A2 | 2/2001 |

* cited by examiner

*Primary Examiner*—John Kim
(74) *Attorney, Agent, or Firm*—Jacobson Holman PLLC

(57) ABSTRACT

A filter device has a housing in the shape of a tubular section, with at least two chambers separated from one another by membranes, and with at least one connection for each flow chamber. The device has two filter caps, with one of each of the filter caps being located on each of the two end regions of the housing, and connected directly or indirectly thereto. All connections for the flow chambers are positioned on the tubular section in order to avoid tolerance variations that frequently occur during installation of the filter device.

14 Claims, 8 Drawing Sheets

FILTERING DEVICE AND A FILTERING DEVICE HOUSING

This is a nationalization of PCT/EP02/08357filed Jul. 26, 2002 and published in German.

BACKGROUND OF THE INVENTION

1. Field of the Invention

The present invention relates to a filter device having a housing, having at least two flow chambers separated from one another by membranes, having at least one connection for each flow chamber, and having at least one filter cap which is placed in the end region of the housing and is connected directly or indirectly thereto. Furthermore, the present invention relates to a housing of a filter device having at least two flow chambers separated from one another by membranes and having at least one end region which is connected to one of the flow chambers and is closable by a filter cap which may be put on the housing.

2. Description of the Prior Art

Filter devices of this type are used extensively in the fields of hemodialysis, hemofiltration, and hemodiafiltration. They typically include a housing in which a fiber bundle is positioned that includes multiple hollow fibers which separate two flow chambers from one another. While blood flows through the passages of the hollow fibers, the fiber outside space delimited by the chamber has dialysate flowing around it. The ends of the fibers are received in casting compounds located in the end regions of the housing. The casting compounds are typically extruded into casting caps in the end region of the housing. After sufficient hardening of the casting compound, the casting cap is removed and the cast cutting is performed, through which the fiber ends are opened. After the fiber ends are cut off, the filter caps are placed on the housing.

In previously known filter devices, each flow chamber is generally provided with two connections, through which the particular medium (blood/dialysate) is supplied and/or removed. These connections are located in the filter caps of the housing, so that the housing does not have any connections. Filter devices are also known in which the connections for the dialysate flowing around the hollow fiber bundle are positioned on the housing and the connections for the blood are positioned in the filter caps. A filter device in which all connections and/or connecting pieces are positioned in the filter caps is known from EP 887 100. In this filter device, all connections are aligned toward one side of the filter device and their center lines run parallel to one another. In this way, it is ensured that the filter device may be connected easily and reliably through plugging in to a filter or dialysis machines and/or a support in such a way that the connections or connecting pieces of the filter device form sealed connections with counter connections or counter connecting pieces.

However, a disadvantage of a filter device of this type is that because of tolerances during the placement of the filter caps on the housing, positioning problems arise as a filter device of this type is connected to the corresponding counterparts. These may lead to an optimal sealed connection not being provided between the connections and/or connecting pieces of the filter device and the corresponding counterparts, which may result in unsatisfactory functioning of the filter device and endangerment of the patient.

In order to avoid problems of this type during the positioning, it is suggested in EP 887 100 that the spacing of the connections of the holding part receiving the filter device be positioned precisely using a centering pin of the holding part in such a way that this spacing corresponds to the spacing of the connections on the filter device. Reliable connection is possible in this way, however, correction of this type is comparatively complex.

A filter device is known from U.S. Pat. No. 4,211,597 which does not include a housing and filter caps placed thereon, but rather two halves which are connected to one another in the lengthwise direction and receive the hollow fiber bundle. During the production of filter devices of this type, the filter housing is manufactured first and the hollow fiber bundle is manufactured separately therefrom in separate work steps. In a further manufacturing step, the hollow fiber bundle is placed in the housing halves and these halves are connected to one another fluid-tight.

It is the object of the present invention to refine a filter device according to the species in such a way that the positioning problems cited during the placement of the filter device on a holder do not occur.

SUMMARY OF THE INVENTION

This object is achieved, starting from a filter device according to the species, in that all connections for the flow chambers are positioned on the housing. The spacing of the connections and/or connecting pieces on the filter device is precisely determined in this way, so that the positioning problems cited may not occur. Tolerance variations during the production of the filter caps or during placement of the filter caps on the housing do not play a role for an optimum connection to the counterparts of a holder.

During the production of the filter device according to the present invention, the casting compound is extruded into the housing, a casting cap being put on which seals the end(s) of the housing. After extrusion of the casting compound and its hardening, this cap is removed and the fiber ends are cut off. The end cap(s) is/are now put on, tolerance variations being decisive neither in this work step nor in the production of the end cap(s) according to the present invention. The spacing of the connections and their alignment is independent of the execution and positioning of the filter caps, since all connections are positioned on the housing according to the present invention.

In a further embodiment of the present invention, the housing is implemented in the shape of a tubular section and two filter caps are provided which are put on both end regions of the housing and connected thereto. The housing is implemented in this case as a hollow cylinder which is sealed in both of its end regions using filter caps. According to the present invention, the filter caps have no connections, since all of these are positioned on the housing.

In a further embodiment of the present invention, two connections are provided for each flow chamber. In this case, one of the connections is used as an inlet for the blood to be purified and/or the fresh dialysate and the particular other connection is used as an outlet for the purified blood and/or the dialysate to be disposed of.

Two connections may be positioned in each of the end regions of the housing, which are positioned one above another or next to one another in the lengthwise direction of the housing. In both cases, one of the connections is connected to the chamber which blood flows through and the particular other connection is connected to the dialysate chamber. This may be achieved, for example, if the connections are received in a projection shaped onto the housing, and if corresponding lines which are connected to the connections and the flow chambers extend inside the projection.

In a further embodiment of the present invention, the connections have connecting pieces which extend in the radial or tangential direction in relation to the housing. For tangential positioning of the connecting pieces, it may be ensured through a corresponding design of the casting compound using blood guiding channels that the blood is distributed largely uniformly over the ends of the hollow fibers.

The blood connecting pieces may be implemented tangentially and discharge into a blood guiding channel extending at least partially around the circumference of the casting compound which encompasses the hollow fiber bundle of the filter device. The blood flows through the blood connecting pieces and subsequently the blood guiding channel, which extends partially around the circumference of the casting compound and using which the blood reaches the cut face of the casting compound and therefore the open ends of the hollow fibers. A tangential embodiment is, of course, also possible for the dialysate connection. In this case as well, a favorable flow of dialysate around the fiber outside space and therefore an optimum material exchange via the membranes may be achieved through suitable arrangement of the connection.

The end regions of the housing may have an enlarged diameter and a freely protruding projection of a smaller diameter which is embedded in the casting compound which receives a hollow fiber bundle. In this way, sealing of the dialysate chamber may be achieved without a further sealing means. The seal is produced by casting the freely protruding projection in the casting compound. The projection may have a force-ejected undercut collar that extends into the casting compound, which is typically made of polyurethane. The projection is typically made of polypropylene. The seal between blood and dialysate sides is performed by precisely pressing the casting compound against the projection through the shrinkage of the cast after its production. The freely protruding projection may be made especially adhesive through a plasma treatment, for example. Besides the cylindrical shape, further geometries, such as a "folded star", are also conceivable.

The filter caps may be glued, welded, or screwed onto the housing.

In a preferred embodiment of the present invention, functional elements are integrated into or onto the housing, using which properties of the media guided through the filter device are detectable and/or changeable or the flow through the filter device may be influenced.

Functional elements of this type may include channels, valves, pumps, measurement chambers, filter and ventilation chambers and membranes. In this way, a highly integrated disposable may be provided which assumes not only the function of filtration, but also further important functions, such as ventilation, filtration, or even pumping. Functional elements of this type were previously generally positioned outside the dialysis disposable, the corresponding numerous connections between the individual components not only requiring complex production and assembly, but also resulting in corresponding seal problems. The functional elements may be positioned in the housing itself or even on the housing. In this way, an injection molded part containing many functions arises. A disposable of this type includes a single main body, and is therefore very material-saving and, particularly because of the connection processes dispensed with, is manufacturing-friendly and user-friendly and additionally seals well.

The housing and the filter caps may be manufactured from polypropylene.

In a further embodiment of the present invention, the connections have connecting pieces whose end regions lie in planes parallel to one another or in a shared plane. Depending on the embodiment of the holder on which the filter device is to be placed, corresponding different arrangements of the connecting pieces may be provided.

The connecting pieces may lie on a shared lengthwise plane or on lengthwise planes parallel to one another.

The present invention also relates to a housing of the filter device having at least two flow chambers separated from another by membranes and having at least one end region which is connected to one of the flow chambers and which is closable by a filter cap which may be put on the housing. Each of the flow chambers has at least one connection and all connections for the flow chambers are positioned on the housing.

The housing is preferably implemented according to one of the aforementioned housing embodiments.

Further details and advantages of the present invention will be described in greater detail on the basis of exemplary embodiments shown in the drawing.

DETAILED DESCRIPTION OF THE PREFERRED EMBODIMENTS

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

Figure 1:
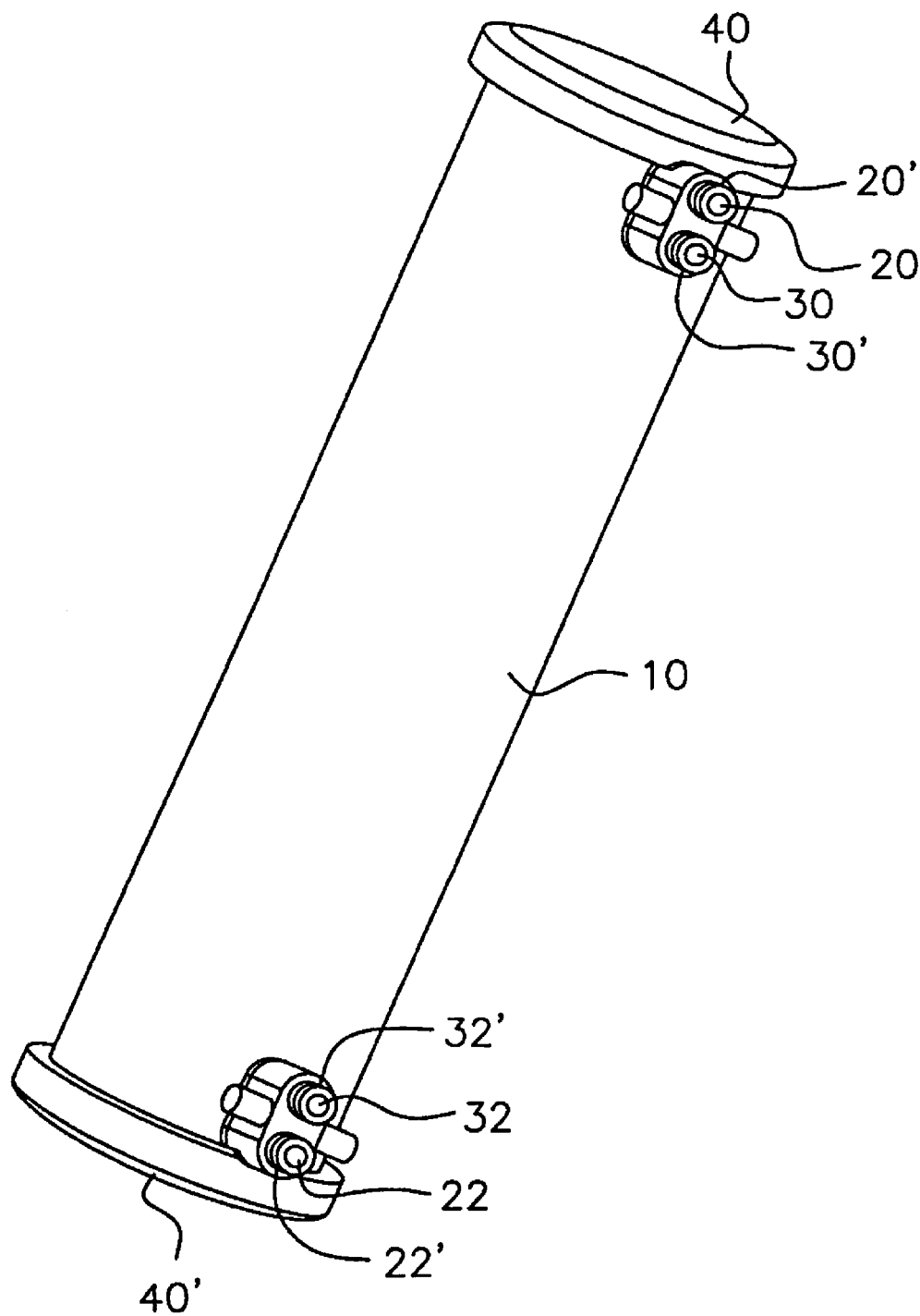
FIG. 1 shows a schematic perspective illustration of a housing of a filter device according to the present invention.

FIG. 1 shows a perspective illustration of the housing 10 of a filter device according to the present invention. The housing 10 is implemented in the shape of a tubular section. The two end regions of the housing are closed using filter caps 40, 40'. The filter caps 40, 40' do not have any connections. The housing 10 has two connections 20, 22 and 30, 32 in each of the two end regions, which are implemented as connecting pieces 20', 22', 30', 32'. Each of the connections 20, 22 are connected to the chamber of the filter device which blood flows through and each of the other connections 30, 32 are connected to the chamber of the filter device which dialysate flows through. The end regions of the connecting pieces 20', 22', 30', 32' are on a shared plane and, in addition, on a shared lengthwise plane. The position of the connections 20, 22, 30, 32 is exactly fixed in the course of the manufacture of the housing 10. When the filter device shown is connected to a corresponding holder of a dialysis unit, precise positioning and therefore a very well sealed connection may be achieved in this way. Positioning problems which arise in previously known achievements of the object using filter caps having connections are avoided in the filter device according to the present invention in that the filter caps do not have connections. Tolerance variations during the production or installation of the filter caps 40, 40' on the housing 10 therefore play no role in the exact connection of the filter device to a holder of a dialysis unit.

A hollow fiber bundle (not shown), which is fixed in the end regions by casting compounds which form a sealed connection to the housing 10, is received in the housing 10. The casting compounds separate the blood chambers, which are delimited by the filter caps 40, 40' and are connected to the connections 20, 22 and to the passages of the hollow fibers, from the fiber outside space, which the dialysate flows through.

Figure 2:
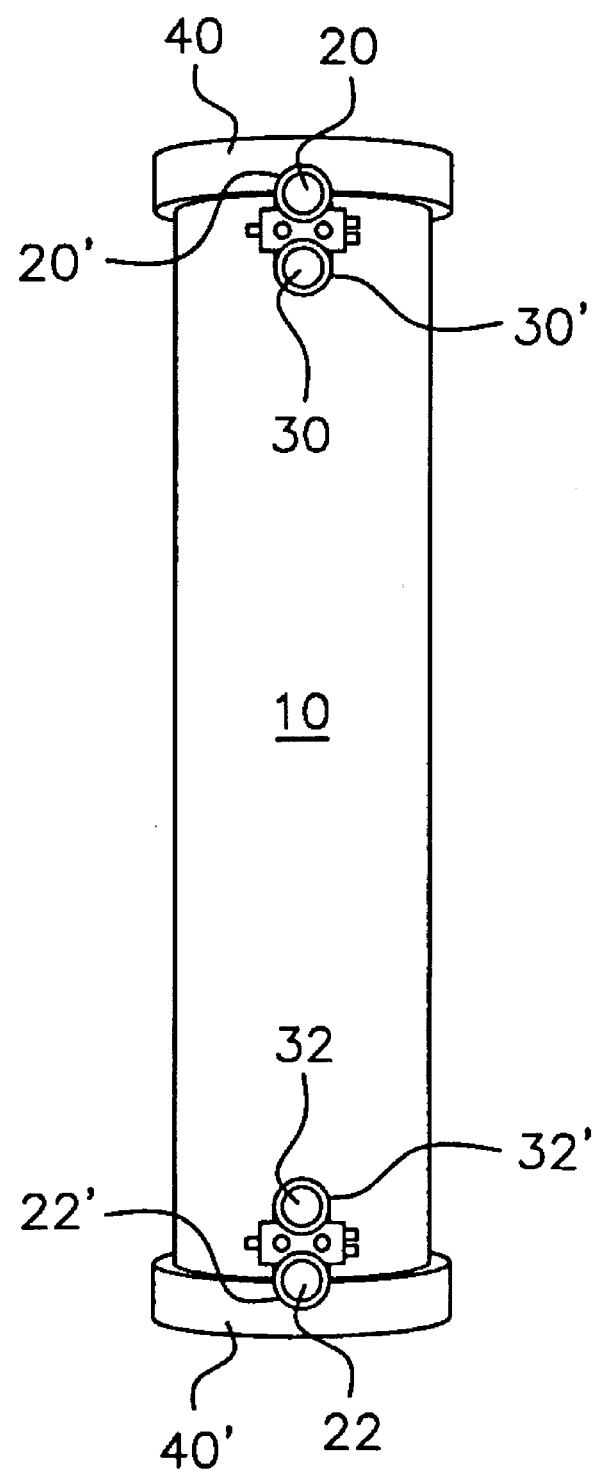
FIG. 2 shows a side view of a filter device according to the present invention.

FIG. 2 shows a side view of a filter device according to the present invention. This filter device corresponds to the one schematically shown in FIG. 1.

Figure 3:
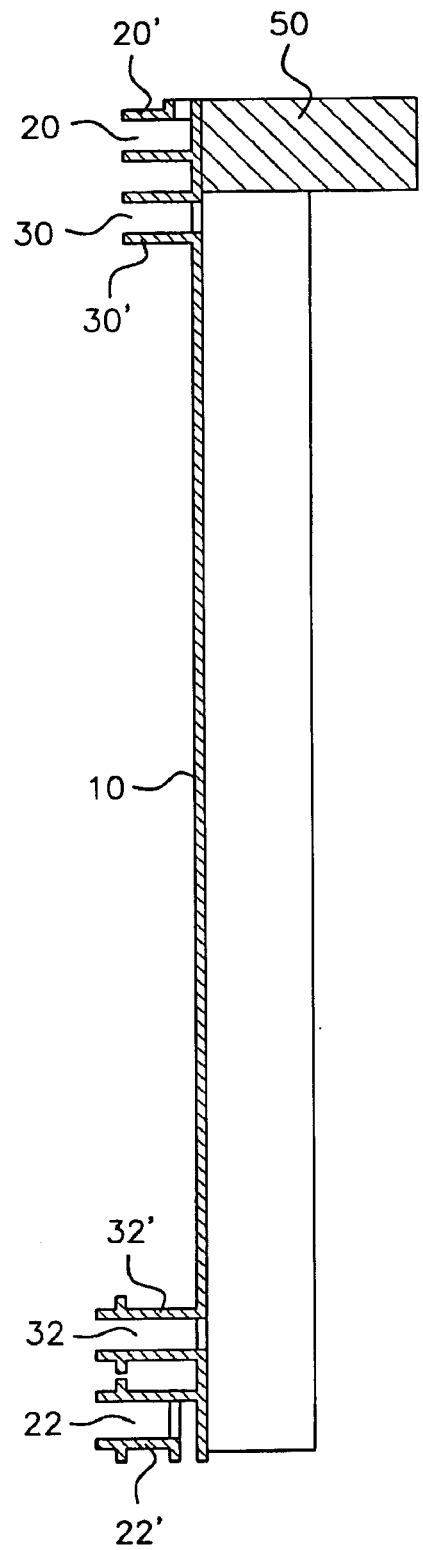
FIG. 3 shows a longitudinal section illustration of a housing of a filter device according to the present invention.

FIG. 3 shows a lengthwise sectional illustration of the positioning of the connecting pieces 20', 22', 30', 32' on the housing 10. The crosshatched region shown on the right in FIG. 3 represents the casting compound 50, which fixes the ends of the hollow fibers. The two connecting pieces 30', 32' distal from the end regions of the housing 10 are used to supply or remove dialysate into or out of, respectively, the fiber outside space enclosing the hollow fiber bundle. The connecting pieces 20', 22' are used to supply and/or remove blood. The blood is introduced into and removed from the filter device through the connections 20, 22 and/or the connecting pieces 20', 22'. These connections are connected to blood chambers which are formed between the filter caps and the casting compound 50 and into which the open ends of the fibers of the hollow fiber bundle discharge.

The connecting pieces 20', 22' may be connected permanently to the housing 10 or even screwed into a corresponding receiver.

Figure 4:
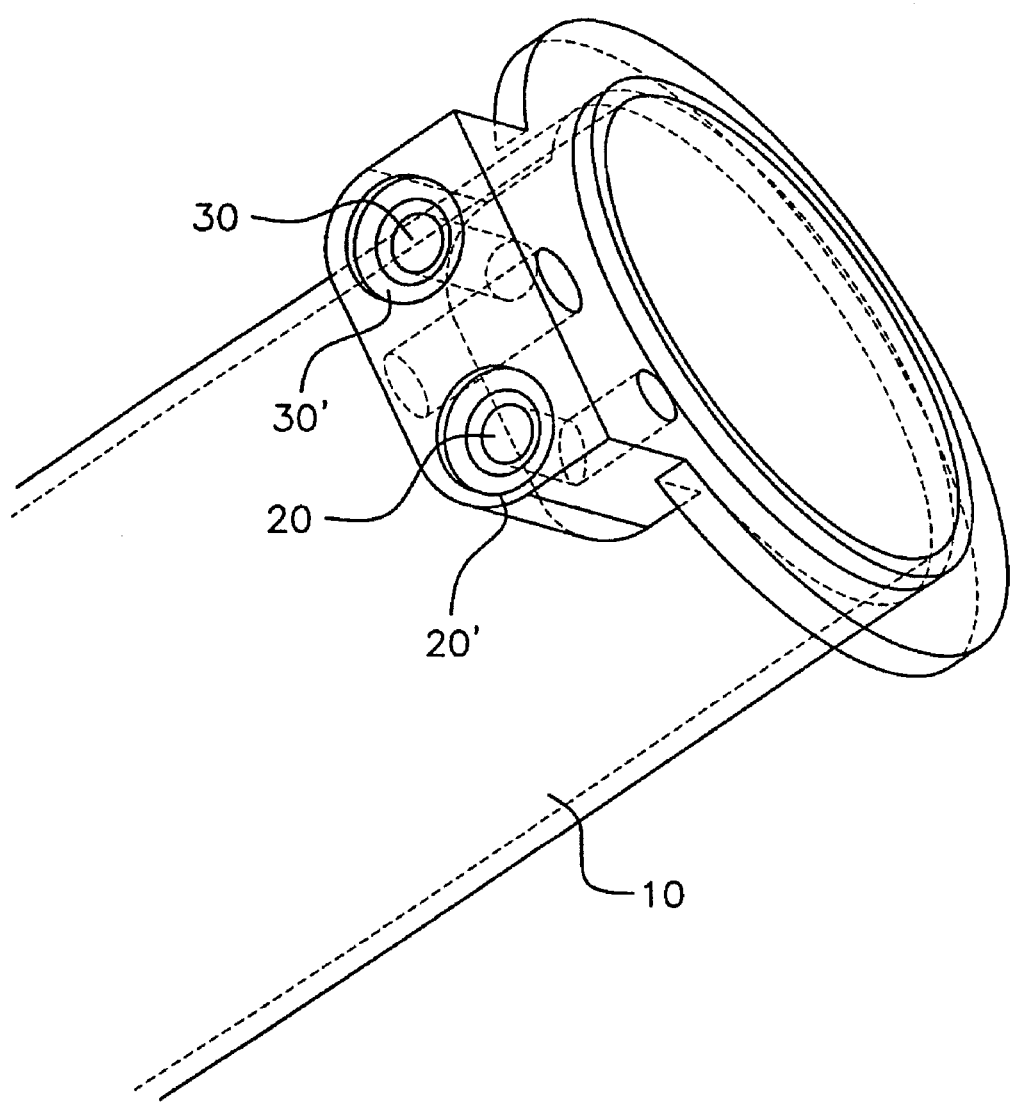
FIG. 4 shows a perspective illustration of a housing of a filter device according to the present invention having connecting pieces positioned next to one another.

An end region of a housing 10 of a filter device according to the present invention, in which the connections 20, 30 and/or the connecting pieces 20', 30' are positioned next one another, is shown in FIG. 4. The connecting pieces 20', 30' are formed here by an attachment positioned on the housing, in which channels extend that connect the connections 20, 30 to the dialysate chamber and to the blood chamber. The end region of the housing 10 has an annular flange on which the filter cap (not shown) is placed and then connected to the housing.

Figure 5:
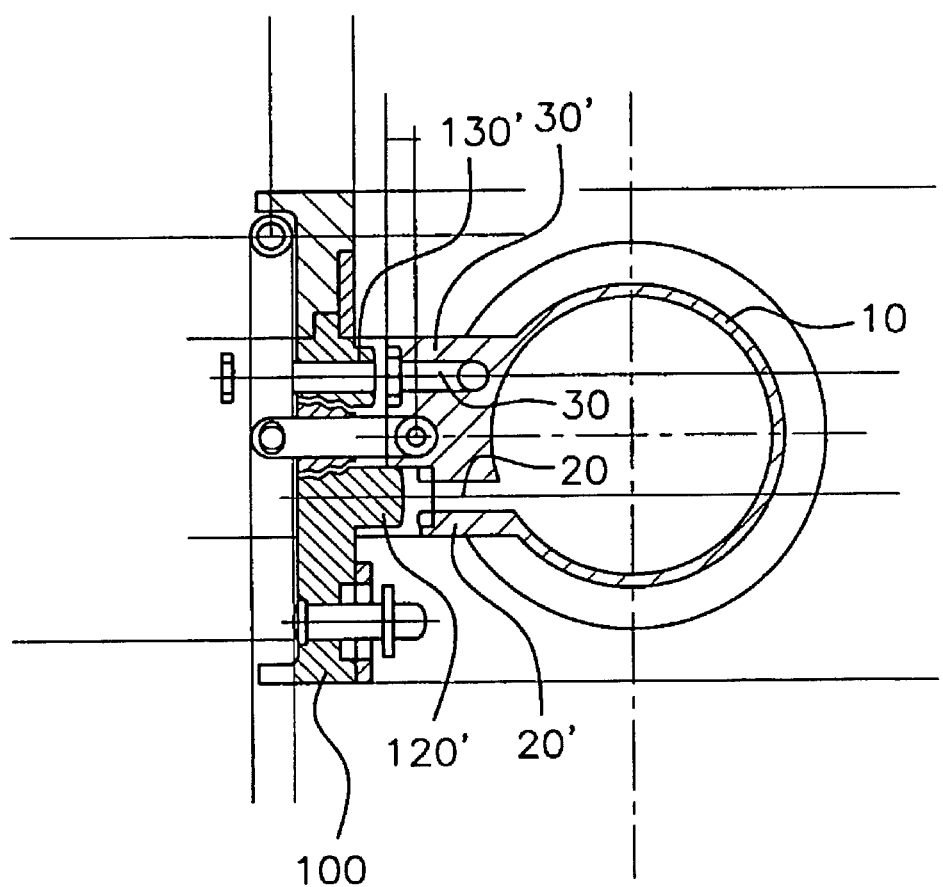
FIG. 5 shows a cross-sectional view of the housing shown in FIG. 4 and a holder of a dialysis machine.

FIG. 5 shows the housing shown in FIG. 4 and a holder of a dialysis unit in a cross-sectional view. The connecting pieces 20', 30' of the housing 10 are connected to corresponding counterparts 120', 130' of the holder 100 to form a seal. Because of the fixed predetermined positioning of the connections and/or connecting pieces on the housing 10, correction devices on the holder, using which the position of the corresponding counterparts 120', 130' must be corrected, are not necessary.

The sealed connection between the connecting pieces 20', 30' and the counterparts 120', 130' is produced in the exemplary embodiment shown in FIG. 5 by O-ring seals received in the connecting pieces 20', 30'.

Figure 6:
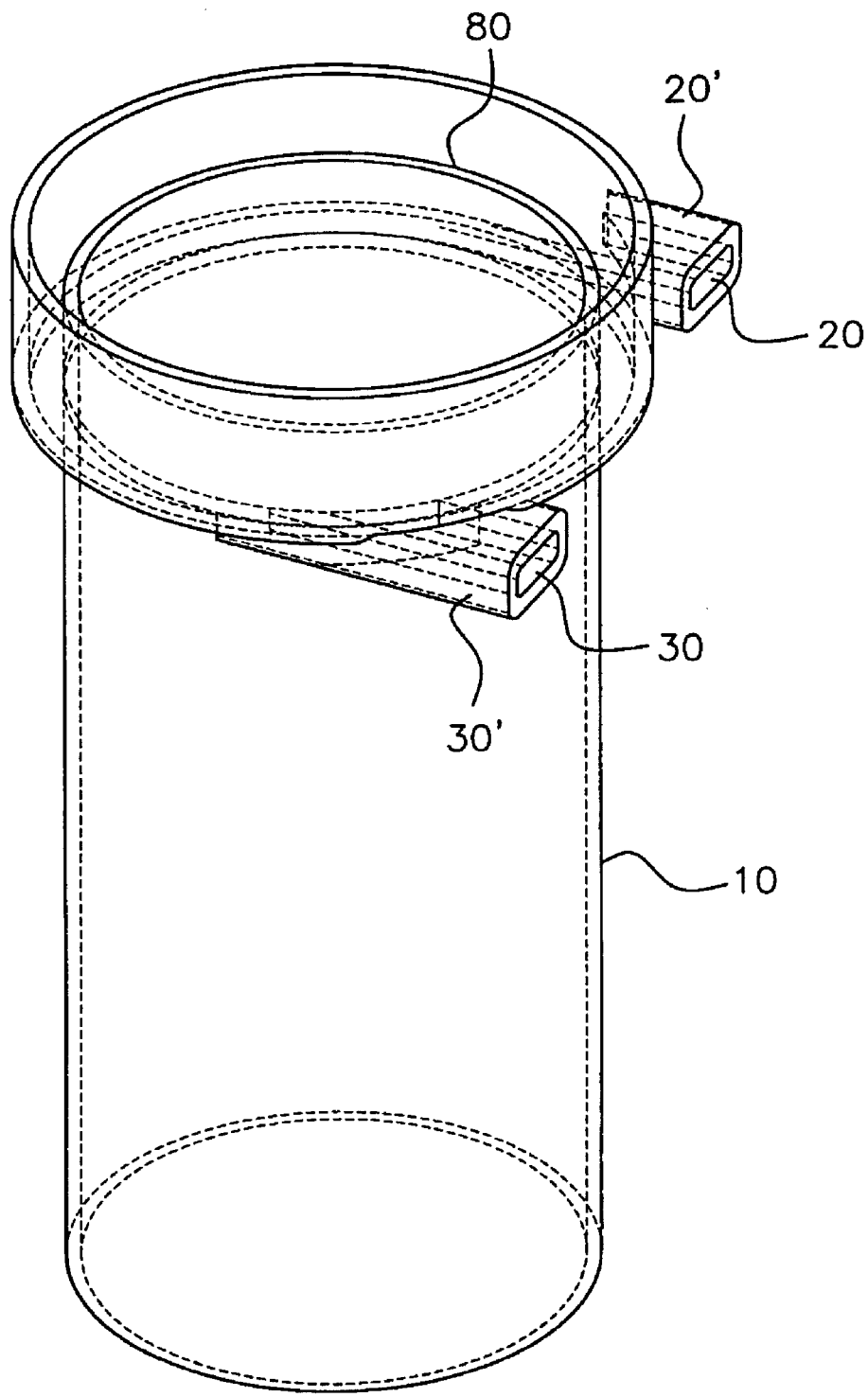
FIG. 6 shows a perspective illustration of an end region of a housing of a filter device according to the present invention having tangentially running connecting pieces.

FIG. 6 shows a perspective illustration of a housing 10 having tangentially implemented connecting pieces 20', 30', which have connections 20, 30, one of which is connected to the side of the filter device that blood flows through and one of which is connected to the side that dialysate flows through. The end region of the housing 10 has an enlarged diameter and a freely protruding, annular projection 80 of a smaller diameter, which is embedded in a casting compound (not shown in FIG. 6) that receives a hollow fiber bundle. This is shown in detail in FIG. 7, FIG. 7, top showing a sectional illustration in the lengthwise direction and FIG. 7, bottom showing a sectional illustration in the transverse traction.

Figure 7:
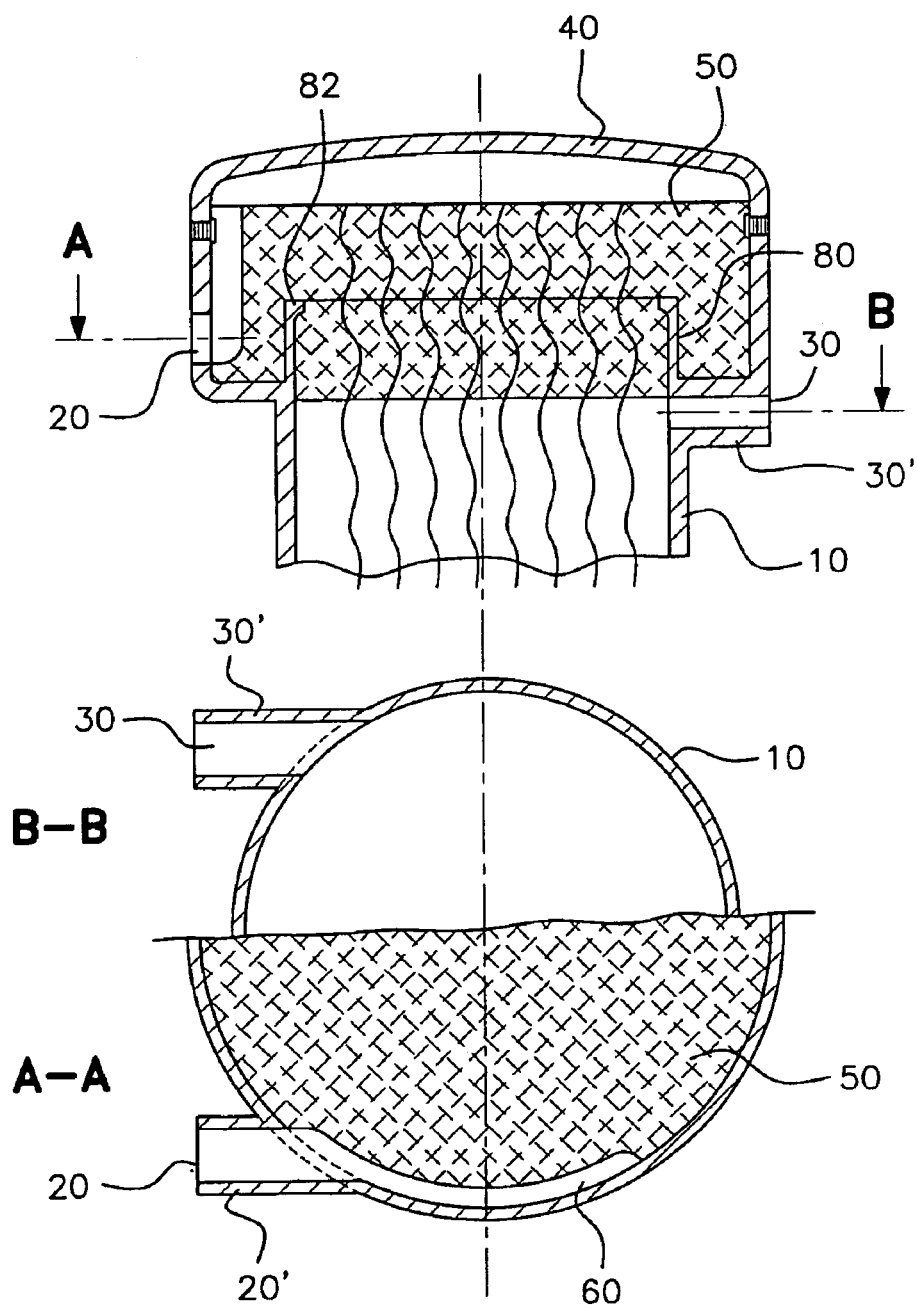
FIG. 7 shows schematic lengthwise and cross-sectional views of an end region of the filter device according to the present invention having tangential connecting pieces.

FIG. 7 shows the filter device in schematic and simplified lengthwise and cross-sectional illustrations. In the lengthwise sectional illustration shown in FIG. 7, top, the outer contours of the filter device are not shown. Furthermore, the connecting piece 20' is not shown in FIG. 7, top.

As may be seen from FIG. 7, top, the annular projection 80 of the housing 10 is embedded in the casting compound 50. The seal between the blood and dialysate sides is produced by pressing the casting compound 50 against the cylindrical region 80. This region has an undercut collar 82, which extends into the casting compound 50. Because of the pre-tension caused by the shrinkage of the casting compound 50, the casting compound 50 presses against the projection 80 to form a seal. The seal between the blood and dialysate sides is produced here only by casting the projection 80 having force-ejected undercut collar 82 into the casting compound 50. The projection 80 may be made more adhesive through plasma treatment. It may include not only the annular shape shown, but also other geometries, such as a "folded star". In contrast to previously known achievements of the object, the seal is not produced through adhesion, but by pressing the casting compound 50 against the projection 80 using the pre-tension caused by the casting shrinkage.

The connecting pieces 20', 30' for blood and dialysate are positioned tangentially on the housing 10, as shown in FIG. 7, bottom. The cross-sectional illustration along line B—B is rotated by 180° in FIG. 7, bottom in relation to the illustration in FIG. 7, top. The section line of the projection 80 is not shown in FIG. 7, bottom (section A—A). A blood guiding channel 60 is positioned in the casting compound 50, which adjoins the blood connecting piece 20' and which produces a connection of the blood connecting piece 20' to the top of the casting compound 50 and therefore to the open end regions of the hollow fibers. In addition, the blood guiding channel 60 may be used for the purpose of distributing the blood supplied as uniformly as possible over the surface of the casting compound 50. For this purpose, the blood guiding channel 60 may be implemented as rising in a spiral shape.

The housing 10 is closed by the filter cap 40, which is connected flush to the housing 10 through a weld. A blood chamber is formed above the casting compound 50 by the filter cap 40, from which the blood is guided into and/or out of the cavities of the hollow fibers.

As may also be seen from FIG. 7, the filter cap 40 has no connections.

Figure 8:
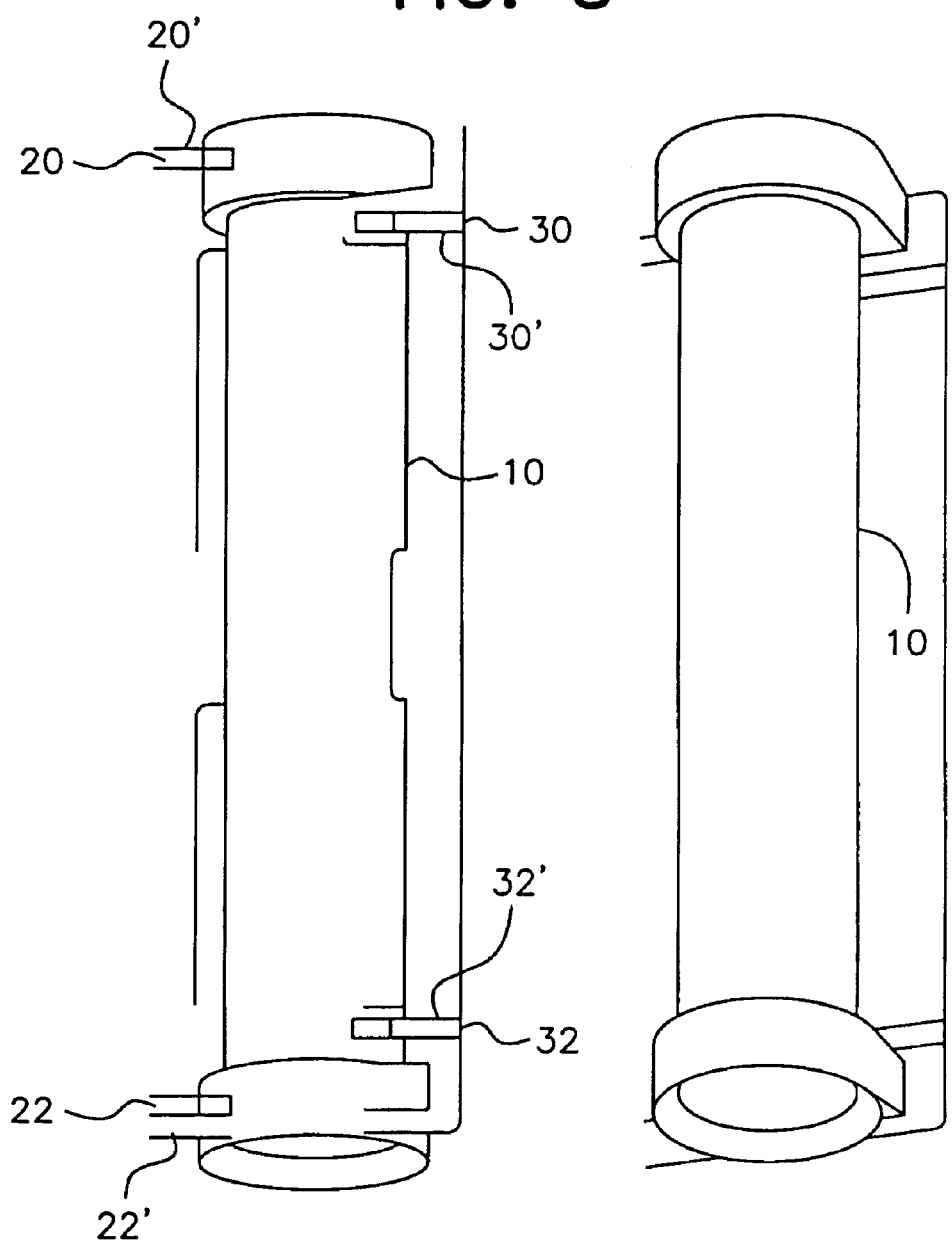
FIG. 8 shows perspective views of a housing of a filter device according to the present invention having tangential connecting pieces.

Finally, FIG. 8 shows perspective illustrations of the housing 10 of the filter device according to the present invention. It is clear once again from these that all connections 20, 22, 30, 32 and/or the corresponding connecting pieces 20', 22', 30', 32' are positioned on the housing 10. The weldable filter caps are used—as noted above—to delimit the blood chambers. In addition, they may have further functional elements such as air separation membranes.

The filter device according to the present invention not only allows simple connection to a holder of a dialysis unit having corresponding counterparts, but additionally allows the provision of a highly-integrated disposable. This may have functional elements, such as pumps, filters, measurement devices, control units, devices for temperature control, ventilation, etc. Because of the positioning of these functional elements in or on the housing, seal problems, which have occurred in previously known achievements of the object during the connection of these functional elements outside the housing, are dispensed with. In previously known achievements of the object, functional elements of this type are integrated into a complex tubing system, which may lead to seal problems because of the numerous connections and, in addition, is complex to produce and operate. In the achievement of the object according to the present invention, this problem may be solved through the integration of the functional elements into and/or on the filter device. For this purpose, no connectors are necessary, so that corresponding production difficulties (assembly, sterilization resistance) are dispensed with.

The further advantage results that the completely automated production of the filter device according to the present invention becomes significantly simpler, since the tolerances play no role for the precision of the connection during the production and/or during the placement of the filter caps. For the same reason, automatic connection of the disposable to the holder of the dialysis machine is made possible, which accordingly results in simpler handling.

The invention being thus described, it will be apparent that the same may be varied in many ways. Such variations are not to be regarded as a departure from the spirit and scope of the invention, and all such modifications as would be recognized by one skilled in the art are intended to be included within the scope of the following claims.

What is claimed is:

1. A filter device comprising:
   a housing having a tubular-shaped section, at least two flow chambers separated from one another by hollow fiber bundle membranes, and at least one connection for each flow chamber, each of the connections being disposed on the tubular-shaped section of the housing; and
   a first filter cap and a second filter cap each disposed on and connected to, respectively, a first end region and a second end region of the tubular-shaped section of the housing.

2. The filter device according to claim 1, wherein two of the connections are provided for each flow chamber.

3. The filter device according to claim 2, wherein two of the connections are positioned in each of the end regions of the housing, which are each positioned one above another or next to one another in a lengthwise direction of the housing.

4. The filter device according claim 1, wherein the connections have connecting pieces extending in the radial or tangential directions in relation to the housing.

5. The filter device according to claim 4, wherein the connecting pieces are implemented tangentially and discharge into a blood guiding channel extending at least partially around a circumference of a casting compound enclosing the hollow fiber bundle membranes.

6. The filter device according to claim 1, wherein the end regions of the housing have an enlarged diameter and a freely protruding projection of a smaller diameter, the protruding projection being embedded in a casting compound enclosing the hollow fiber bundle membranes.

7. The filter device according to claim 1, wherein the filter caps are glued, welded, or screwed on the housing.

8. The filter device according to claim 1, wherein the housing includes functional elements integrated into or onto the housing, the functional elements being capable of detecting and/or changing properties of a medium flowing through the filter device, or of influencing the flow of the medium.

9. The filter device according to claim 1, wherein the housing and the filter caps are of polypropylene construction.

10. The filter device according to claim 1, wherein the connections have connecting pieces with end regions lying in planes parallel to one another or in a shared plane.

11. The filter device according to claim 1, wherein the connections have connecting pieces lying on a shared lengthwise plane or on lengthwise planes parallel to one another.

12. A housing of a filter device comprising:
   a tubular-shaped section having at least two flow chambers separated from one another by hollow fiber bundle membranes and having two end regions, each of the end regions being connected to one of the flow chambers and being closable by a filter cap capable of being placed on the tubular-shaped section; and
   at least one connection in communication with each flow chamber, each of the connections being positioned on the tubular-shaped section.

13. The housing according to claim 12, wherein two of the connections are provided for each flow chamber.

14. The housing according to claim 12, wherein the housing includes functional elements integrated into or onto the housing, the functional elements being capable of detecting and/or changing properties of a medium flowing through the filter device, or of influencing the flow of the medium.

* * * * *